United States Patent [19]

Arakawa et al.

[11] Patent Number: 4,565,779
[45] Date of Patent: Jan. 21, 1986

[54] PHOTOCHROMIC COMPOUNDS AND PHOTOSENSITIVE COMPOSITIONS CONTAINING THE COMPOUNDS

[75] Inventors: Seiichi Arakawa, Chigasaki; Hirofumi Kondo; Junetsu Seto, both of Yokohama, all of Japan

[73] Assignee: Sony Corporation, Tokyo, Japan

[21] Appl. No.: 565,201

[22] Filed: Dec. 23, 1983

[30] Foreign Application Priority Data

Dec. 28, 1982 [JP] Japan .................... 57-233036

[51] Int. Cl.$^4$ .............. G03C 1/52; G03C 1/733
[52] U.S. Cl. ...................... 430/962; 549/24; 549/25
[58] Field of Search .............. 549/24, 25; 430/962

[56] References Cited

U.S. PATENT DOCUMENTS 4,237,207 12/1980 Ceintrey ................. 430/962
4,485,168 11/1984 Arakawa et al. ........... 430/962

Primary Examiner—John Kight
Assistant Examiner—M. L. Moore
Attorney, Agent, or Firm—Hill, Van Santen, Steadman & Simpson

[57] ABSTRACT

Novel photochromic compounds are disclosed, which compounds are represented by the general formula

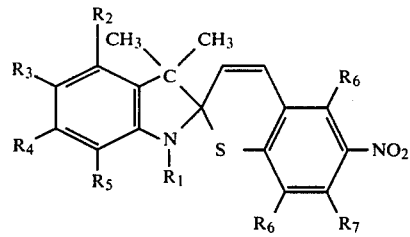

in which $R_1$ represents an alkyl group having 1 to 20 carbon atoms, $R_2$, $R_3$, $R_4$ and $R_5$ independently represent an alkyl group having 1 to 5 carbon atoms, an alkoxy group having 1 to 5 carbon atoms, a halogen atom, a nitro group, a cyano group or a dimethylamino group, and $R_6$, $R_7$ and $R_8$ independently represent a hydrogen atom, an alkyl group having 1 to 5 carbon atoms, an alkoxy group having 1 to 5 carbon atoms, or a halogen atom, and correspondingly 97 to 50 wt % of a film-forming polymer. Photosensitive compositions and materials comprising the compounds are also described.

4 Claims, No Drawings

PHOTOCHROMIC COMPOUNDS AND PHOTOSENSITIVE COMPOSITIONS CONTAINING THE COMPOUNDS

BACKGROUND OF THE INVENTION

1. Field of the Invention:

This invention relates to the optical recording art and more particularly, to novel photochromic compounds. Also, it relates to photosensitive compositions and materials comprising such compounds.

2. Description of the Prior Art:

Photochromic photosensitive spiropyran materials are known to have a number of advantages: (1) high resolution is obtained without involving any particulate property; (2) no specific developing and fixing treatments are needed; (3) thin film formation is possible because of high intensity of formed color; and (4) erasion and rewriting are possible. Accordingly, attempts have been made to apply these materials to various recording and memory materials and also to duplicating materials. Especially in recent years, application of these materials as recording media, e.g. optical video discs, in which a laser beam is used to record and reproduce information signals while making use of the features (1) and (4) indicated above, is highly expected.

Known photochromic, photosensitive spiropyran materials have an absorption wavelength, in colored state, ranging at most from 400 nm to 700 nm. For laser beam recording or reproducing purposes, it is essential to use a gas laser such as $Ar^+$ or He—Ne laser. As is well known, small-size, light-weight semiconductor lasers have recently been developed markedly. So, semiconductor lasers tend to take the place of gas lasers for recording and reproducing purposes.

Semiconductor lasers which are actually applied for laser recording or reproducing operations are those whose emitting wavelength ranges from 780 to 850 nm. At present, semiconductor lasers which emit at shorter wavelengths have been extensively developed. It is considered that there is the high possibility of putting into practice semiconductor lasers emitting at about 700 nm in a very near future (see, for example, "Present State and Future of Semiconductor Laser Recording", Journal of Japanese Photographic Association 44 (2) (1981), by Fujitaro Saito, and "Development and Present State of Visible Light Semiconductor Lasers", Optionics (No. 9), 41 (1982).

In order to apply photochromic photosensitive spiropyran materials as a recording medium for semiconductor laser recording and reproducing purposes, the materials should have good absorption characteristics with respect to light having a wavelength higher than as in prior art cases and particularly a wavelength higher than 700 nm.

As is known in the art, the following spirothiopyran compound has a good absorption characteristic, in colored state, against light having such a range of wavelength as mentioned above (see J. Phys. Chem. 72, 997 (1981), by H. S. Becker and J. Kolc).

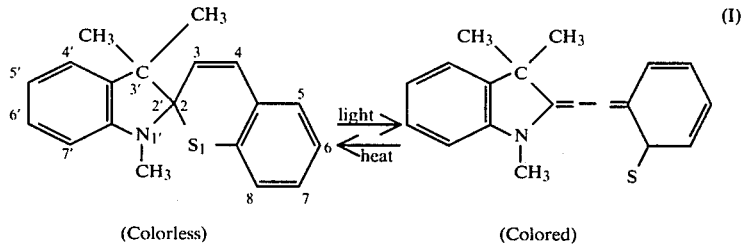

(Colorless)    (Colored)

Although this compound has a high absorption characteristic in colored state with respect to light having a wavelength ranging from 600 to 850 nm when placed in a 3-methylpentane solution at 77° K, it does not form any color at a normal temperature even in solution or polymer film. The compound is able to develop a color only at temperatures lower than 0° C. and the once developed color disappears immediately after returning to a normal temperature. Thus, this compound cannot be practically used.

SUMMARY OF THE INVENTION

It is accordingly an object of the present invention to provide novel photochromic compounds which have a high absorption characteristic against light having a wavelength higher than 700 nm.

It is another object of the invention to provide photochromic compounds which are stable in color formation.

It is a further object of the invention to provide photochromic compounds which are able to repeat color formation and bleaching depending on the temperature and the UV irradiation.

It is a still further object of the invention to provide photochromic compounds which ensure recording by semiconductor laser.

It is another object of the invention to provide photochromic compositions comprising photochromic compounds of the just-mentioned type.

The above objects can be achieved, according to the present invention, by a novel photochromic compound of the general formula

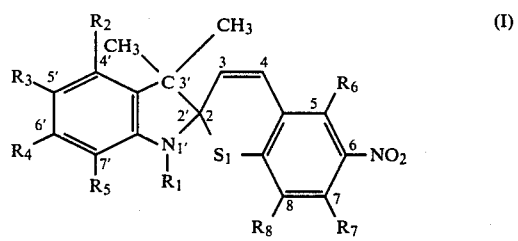

in which $R_1$ represents an alkyl group having 1 to 20 carbon atoms, $R_2$, $R_3$, $R_4$ and $R_5$ independently represent an alkyl group having 1 to 5 carbon atoms, an alkoxy group having 1 to 5 carbon atoms, a halogen atom, a nitro group, a cyano group or a dimethylamino group, $R_6$, $R_7$ and $R_8$ independently represent a hydrogen, atom, an alkyl group having 1 to 5 carbon atoms, an alkoxy group having 1 to 5 carbon atoms, or a halogen atom. Preferably, in the formula (I), $R_1$ is an alkyl group having 1 to 10 carbon atoms, and $R_2$ and $R_4$ through $R_8$ independently represent a hydrogen atom. The preferable compounds are represented by the following general formula

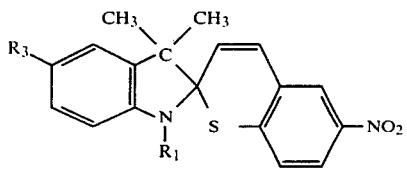

in which $R_1$ represents an alkyl group having 1 to 10 carbon atoms and $R_3$ represents a hydrogen atom, a halogen atom, an alkyl group having 1 to 5 carbon atoms, an alkoxy group having 1 to 5 carbon atoms, a nitro group, a cyano or dimethyl amino group.

Specific examples of the novel photochromic compound are indicated in examples and Table 1 appearing hereinafter.

The present invention also provides a photochromic composition which comprises a mixture of 50 to 97 wt. % of a film-forming polymer and correspondingly 50 to 3 wt. % of a photochromic compound of the formula (I).

DETAILED DESCRIPTION AND EMBODIMENTS OF THE INVENTION

The photochromic compounds of the present invention are prepared according to the following reaction formula (A)

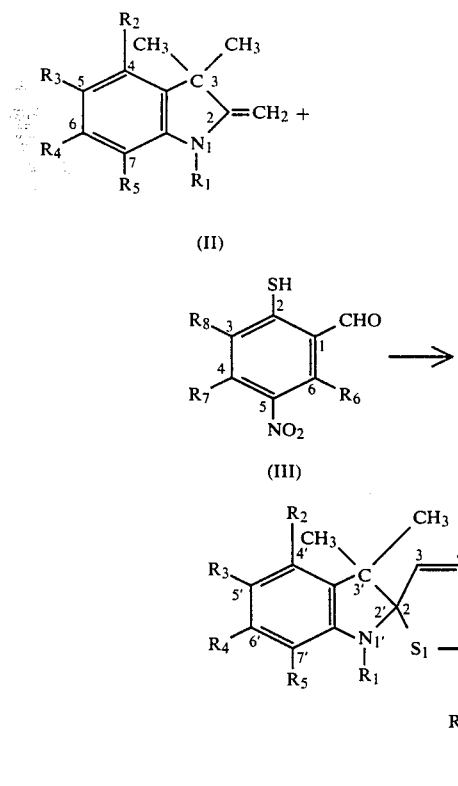

In other words, the novel compound of the formula (I) of the invention can be prepared readily and in high yield by refluxing, in ethanol, 1-alkyl-3,3-dimethyl-2-methyleneindoline (II) and 5-nitrothiosalicylaldehyde (III).

The starting compound (II) is prepared, according to the reaction formula (B), by alkylating 2,3,3-trimethylindolenine (IV) at N position thereof with an alkyl halide $R_1X$ in which X represents a halogen atom, thereby forming a salt (V), and subsequently treating the salt with an alkali.

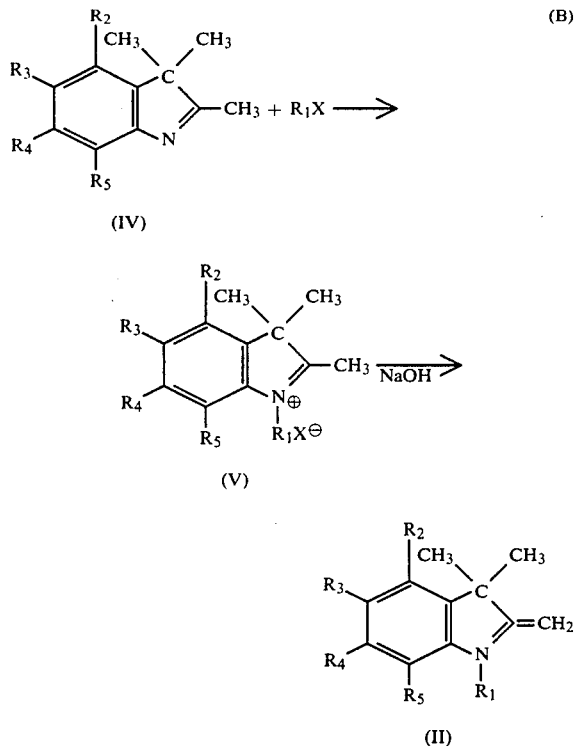

For the alkylation at the N position, dialkylsulfates, alkyl toluenesulfonates and the like may also be used.

When $R_3$ in compound (II) is $(CH_3)_2N-$, i.e. the compound (II) is 5-dimethylamino-1,3,3-trimethyl-2-methyleneindoline, it is necessary to use a specific technique for its preparation. This preparation process was first found by us. The compound is prepared according to the following reaction formula (C) in which 5-amino-2,3,3-trimethylindolenine is reacted with methyl iodide in the presence of a hindered amine, e.g. 1,2,2,6,6-pentamethylpiperidine to obtain a quaternary amine, and heating for demethylation the quaternary amine along with sodium n-propyl alcoholate. This is particularly described in Example 5 appearing hereinafter.

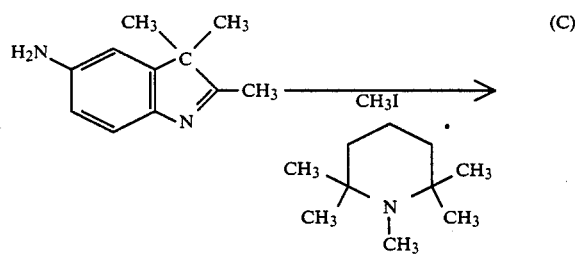

-continued

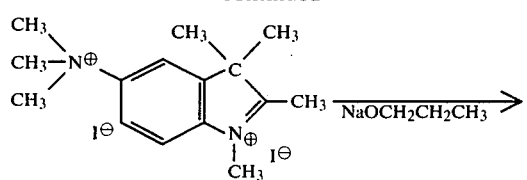

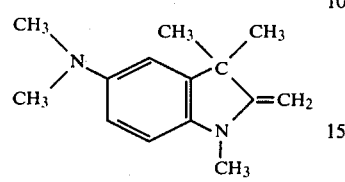

The compound (I) of the present invention which is prepared according to the reaction formula (A) using a compound (II) in which $R_3$ is a dimethylamino group has such a feature that it is very stably colored by UV irradiation.

The afore-indicated 2,3,3-trimethylindolenine (IV) can be ordinarily obtained on the basis of the Fischer's indole synthesis in which a substituted phenylhydrazine or hydrochloride thereof and 3-methyl-2-butanone are heated under acidic conditions. Alternatively, substituted aniline and 3-methyl-3-bromo-2-butanone may be heated to obtain the compound (IV). Part of this preparation process is novel and is particularly described in Example 3.

Preparation of 5-nitrothiosalicylaldehyde (III) used in the reaction (A) is not known. This compound (III) can be prepared according to the reaction formula (D) or (E).

(1) Method of converting a halogen atom of an aldehyde compound carrying a halogen atom at the ortho position into SH group (see Example 1):

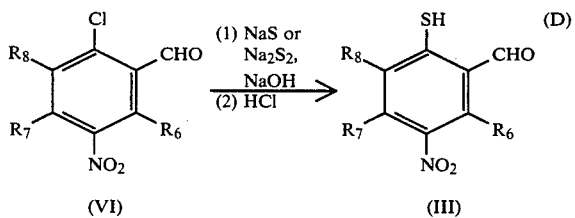

This reaction readily proceeds when $R_6$, $R_7$ and $R_8$ are independently a hydrogen atom (such compound being readily available), but synthesis of 5-nitrothiosalicylaldehyde having substituents is very difficult. In the case, the method using the following reaction formula (E) is used.

(2) Method of converting OH group of salicylaldehyde into SH group:

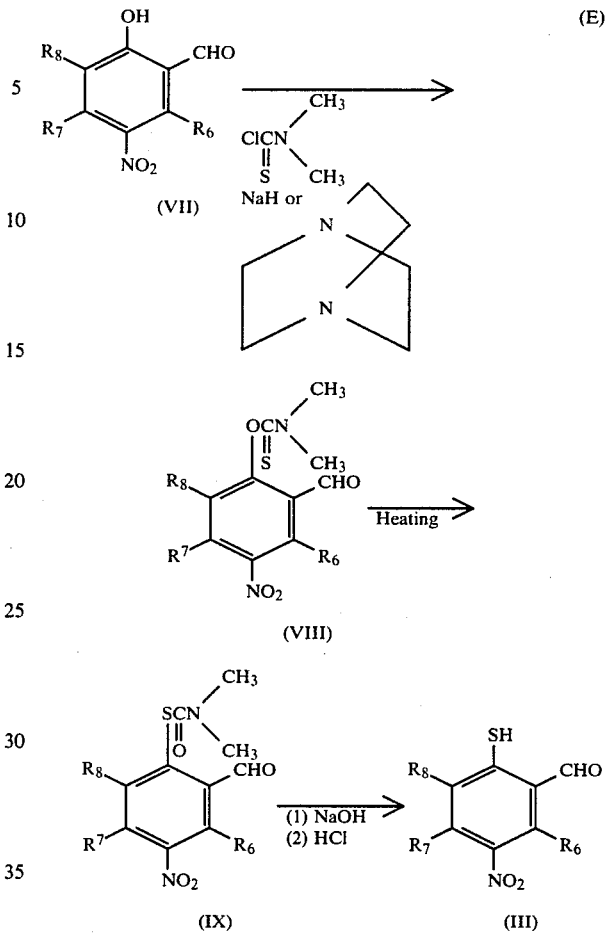

Dimethylcarbamate (VIII) is prepared from the salicylaldehyde (VII), followed by heating for causing the rearrangemnt reaction of O and S to obtain a compound (IX) and subsequent alkali hydrolysis to give thiosalicylaldehyde (III). The series of the reactions are known per se. However, it is not known to apply these reactions so as to obtain a structure of the compound (III). These reaction (E) are advantageous in that synthesis of the starting salicylaldehyde is easy and yields at the respective reaction stages are high. Accordingly, for the synthesis of 5-nitrosalicylaldehyde having substituents, it is favorable to use the process (E). In the process, the reaction can be caused to proceed so that compound (VII) can be converted into compound (IX) at a time as will be seen in Example 4.

The photochromic, photosensitive compounds or materials of the present invention which has been once colored may be bleached or returned to its original colorless state by heating to 60° to 80° C. or by irradiation of visible light having a wavelength higher than 500 nm. UV irradiation enables the material to be colored. Thus, the material can stand repeated use.

These compounds have very wide utility in various fields. For instance, they are used as a medium for semiconductor laser recording and reproducing purposes and also as various recording materials such as memory materials, duplication materials, photosensitive materials for printing, recording materials for cathode ray tube, photosensitive materials for holography. Also, the materials can be utilized as materials for optical filter, display, masking, actionometer, decoration and the like.

The photochromic compounds of the invention are soluble in various solvents including alcohols such as methanol, ethanol, isopropyl alcohol and the like, ketones such as acetone, methyl ethyl ketone, cyclohexanone and the like, ethers such as ethyl ether, dioxane, tetrahydrofuran and the like, esters such as ethyl acetate, n-butyl acetate and the like, benzene, toluene, xylene, n-hexane, cyclohexane, acetonitrile, dimethylformamide, dimethylsulfoxide, chloroform, and mixtures thereof. When the compound is applied as a photochromic material or medium, it is dissolved in solvent along with a polymer material. The resulting solution is used for film formation or applied onto a support and dried. Alternatively, the compound may be kneaded along with a polymer material without use of any solvent and subjected to film formation.

The polymer materials useful in the practice of the invention may be any materials which are miscible with of the compounds of the general formula (I) and which have excellent film-forming ability. Examples of such polymers include polymethyl methacrylate, polystyrene, polyvinyl acetate, polyvinylbutyral, cellulose acetate, polyvinyl chloride, polyvinylidene chloride, vinyl chloride-vinyl acetate copolymer, polypropylene, polyethylene, polyacrylonitrile, urethane resins, epoxy resins, polyesters, phenolic resins, phenoxy resins, and the like. Of these, chlorine-containing polymers are preferable because of higher stability after color formation. The amount of the compound represented by the general formula (I) in a photosensitive composition comprising a polymer materials is generally in the range of from 3 to 50 wt. %, preferably from 5 to 30 wt. %. Amounts smaller than 3 wt. % are unfavorable because it gives lower optical density. On the other hand, amounts larger than 50 wt. % result in precipitation of the compound (I) from polymer material.

The present invention is particularly described by way of examples.

EXAMPLE 1

Preparation of 1',3',3'-trimethyl-6-nitrospiro-[2H-1-benzothiopyran-2,2'-indoline]

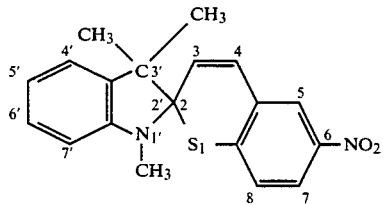

5-nitrothiosalicylaldehyde of the following formula,

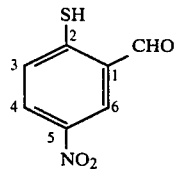

which is one of starting materials, was prepared according to the following reaction formulas

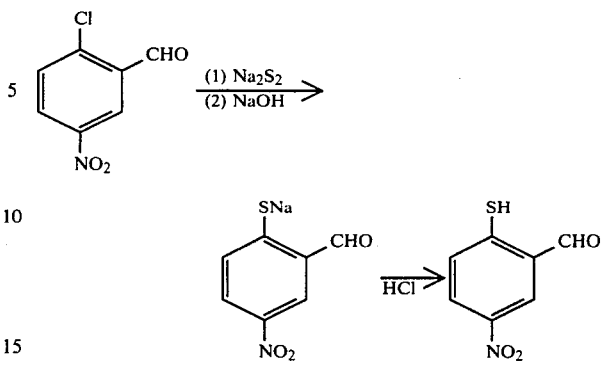

5 g of 2-chloro-5-nitrobenzaldehyde was added to 10 cc of ethanol, followed by heating under refluxing conditions. Thereafter, a mixture of 4.66 g of $Na_2S.9H_2O$ and 0.62 g of S was heated to obtain $Na_2S_2$. The thus obtained $Na_2S_2$ was added to a boiled 2-chloro-5-nitrobenzaldehyde solution in ethanol in 15 minutes. After completion of the addition, 10 cc of a 95% ethanol solution containing 1.08 g of NaOH was further added in 30 minutes. After completion of the addition, the mixture was cooled and poured into iced water consisting of 30 g ice and 400 cc of water, followed by filtering insoluble matters. The resulting filtrate was neutralized with HCl, thereby obtaining a yellow precipitate. The precipitate was collected by filtration. Since the yellow precipitate contained impurities, it was dissolved in 20 cc of ethanol while heating, to which was added a 95% ethanol solution containing 1.08 g of NaOH, followed by removing insoluble matters by filtration. The filtrate was again neutralized with HCl and cooled to obtain yellow crystals of intended 5-nitrothiosalicylaldehyde. The crystals were collected by filtration and dried for use in subsequent reaction. The yield was 3.15 g (64%) and the melting point was 85°–88° C.

Thereafter, 1.6 g of commercially available 1,3,3-trimethyl-2-methyleneindoline and 2 g of the 5-nitrothiosalicylaldehyde obtained in a manner as described above were placed in 100 cc of methanol and heated under refluxing conditions for 2 hours. The solution was concentrated, to which was added methanol, thereby precipitating yellow crystals. The crystals were recrystallized from benzene-methanol to obtain intended 1',3',3'-trimethyl-6-nitrospiro[2H-1-benzothiopyran-2,2'-indoline]. The yield was found to be 1.1 g (35%) and the melting point was 178°–179° C.

The 5-nitrothiosalicylaldehyde prepared as the starting material was analyzed by the proton-NMR spectroscopy. TMS (tetramethylsilane) was used as an internal standard and $CDCl_3$(chloroform-$d_1$) was used as a solvent. The measurement was effected by the use of JNM-FX60Q NMR apparatus made by Nippon Electronics Co., Ltd. The results are shown below with the compound being identified.

Chemical Shift ($\delta$, ppm)
6.16 (singlet, SH, 1H)
7.48 (doublet, H at 3 position, 1H)
8.22 (double doublet, H at 4 position, 1H)
8.61 (doublet, H at 6 position, 1H)
10.10 (singlet, CHO, 1H)

Likewise, the 1',3',3'-trimethyl-6-nitrospiro-[2H-1-benzothiopyran-2,2'-indoline] was subjected to spectroscopic measurement in the same manner as described above and identified by the following proton-NMR spectrum data.

δ (ppm)
1.24 (singlet, C—CH₃, 3H)
1.40 (singlet, C—CH₃, 3H)
2.64 (singlet, N—CH₃, 3H)
5.96 (doublet, H at 3 position, 1H)
6.44 (doublet, H at 7' position, 1H)
6.6–7.4 (multiplet, aromatic H, H at 4 position, 5H)
7.7–8.1 (multiplet, H at 5,7 positions, 2H)

A solution of 3 parts by weight of the thus obtained 1',3',3'-trimethyl-6-nitrospiro[2H-1-benzothiopyran-2,2'-indoline] and 10 parts by weight of vinyl chloride-vinylidene chloride copolymer (Denka Vinyl #1000W, by Denki Chem. Ind. Co., Ltd.) as a polymer material in 100 parts by weight of a solvent (tetrahydrofuran:cyclohexanone=1:1 (by volume)) was prepared. The solution was spinner coated onto a quartz substrate and dried at 80° C. for 2 hours to obtain a sample having a 1.5 micron thick photosensitive layer.

The thus obtained sample was exposed to ultraviolet light having a wavelength of about 360 nm from a 500 W super high pressure mercury lamp (Ushio Electrical Machinery Co., Ltd.) through a glass filter (UV-D360, by Toshiba Corp.). The light yellow sample was changed to dark green in color. The absorption spectra were measured by the self-recording spectrophotometer Model 320 made by Hitachi, Ltd. It was found that the sample which had irradiated with UV light had a maximum absorbance at 680 nm and the absorption extended to about 900 nm. The maximum absorbance at the wavelength of 680 nm was about 0.6. The same had a significant absorption at 780 nm and the rate of the absorbance based on the absorbance at the absorption maximum wavelength (λ$_{max}$) was 47%.

For comparison, the above procedure was repeated using 1',3',3'-trimethyl-6-nitrospiro[2H-1-benzopyran-2,2'-indoline] which was a known spiropyran compound. The resulting photosensitive film was used to determine its color formation characteristic. As a result, it was found that λ$_{max}$ was 580 nm and an absorption end at a long wavelength side was 700 nm.

EXAMPLE 2

Preparation of 5'-methoxy-1'-n-hexyl-3',3'-dimethyl-6-nitro-8-methoxyspiro[2H-1-benzothiopyran-2,2'-indoline]

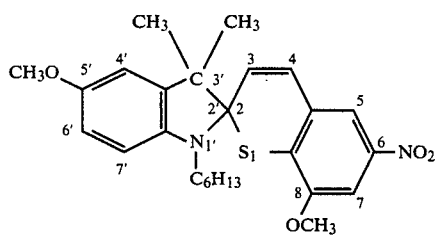

3-methoxy-5-nitrothiosalicylaldehyde of the following formula, which was one of starting materials,

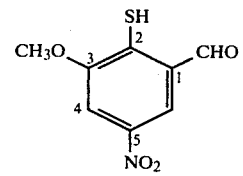

was prepared in the following manner. 10 g of 3-methoxy-5-nitrosalicylaldehyde and 11.4 g of 1,4-diazabicyclo[2,2,2]octane were dissolved in DMF (dimethylformamide). To the solution was added a solution of 9.4 g of dimethylthiocarbamoyl chloride in DMF, followed by reacting at 50°–60° C. for 1.5 hours. Thereafter, 300 cc of water was added to the reaction solution and resulting precipitate was filtered, followed by recrystallizing from methanol to obtain 11.1 g (yield 77%) of dimethylthiocarbamate

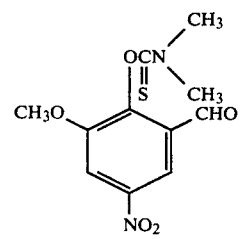

This dimethylthiocarbamate was heated on an oil bath of 160° C. and melted, after which it was cooled and admixed with methanol. The resulting crystals were filtered to obtain 10.3 g (yield 93%) of a compound of the following formula

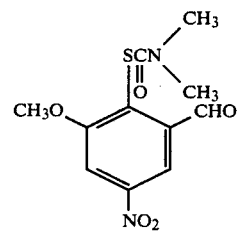

The compound was dissolved in 300 cc of methanol, to which was added 30 cc of an aqueous 4N NaOH solution at a normal temperature, followed by reaction for 1 hour while blowing N₂ gas into the reaction system. Concentrated hydrochloric acid was subsequently added to the reaction system to render the system acidic, followed by refluxing for 40 minutes, cooling, adding 100 cc of water, and filtering the resulting crystals, thereby obtaining 7.65 g 'yield 99%) of 3-methoxy-5-nitrothiosalicylaldehyde. The melting point was 169°–170° C. The compound was subjected to the proton-NMR spectroscopy in the same manner as in Example 1 with the results shown below. From the above result, the compound was identified as intended.

δ(ppm)
4.09 (singlet, OCH₃, 3H)
6.10 (singlet, SH, 1H)
7.85 (doublet, H at 4 position, 1H)
8.31 (doublet, H at 6 position, 1H)
10.41 (singlet, CHO, 1H)

Subsequently, 4.6 g of the thiosalicylaldehyde and 5.9 g of 1-n-hexyl-3,3-dimethyl-5-methoxy-2-methyleneindoline of the following formula (which was obtained by reacting 5-methoxy-2,3,3-trimethylindolenine and hexyl bromide in chloroform and treated the resulting product with NaOH)

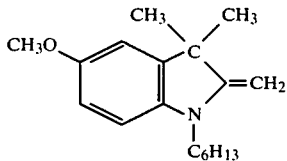

were heated and refluxed in 100 cc of ethanol for 2 hours. The solution was concentrated and subjected to isolation by silica gel column chromatography, followed by recrystallization with benzene-methanol to obtain 4.6 g of intended 5'-methoxy-1'-n-hexyl-3',3'-dimethyl-6-nitro-8-methoxyspiro[2H-1-benzothiopyran-2,2'-indoline]. The yield was 45% and the melting point was 97°–98° C.

¹H-NMR Spectrum Data

δ (ppm)

0.88 (triplet, n-hexyl group, CH₃, 3H)
1.23 (singlet, C—CH₃, 3H)
1.36 (singlet, C—CH₃, 3H)
1.0–2.0 (multiplet, n-hexyl group, CH₂, 8H)
3.04 (triplet, N—CH₂, 2H)
3.77 (singlet, OCH₃, 3H)
3.90 (singlet, OCH₃, 3H)
5.94 (doublet, H at 3 position, 1H)
6.40 (doublet, H at 7' position, 1H)
6.5–6.8 (multiplet, H at 4',6' positions, 2H)
6.84 (doublet, H at 4 position, 1H)
7.52 (doublet, H at 7 position, 1H)
7.74 (doublet, H at 5 position, 1H)

The compound of this example was dissolved in DMF and degassed. Upon irradiation of ultraviolet light at about 360 nm, the solution was colored in green. When the colored solution was heated, the solution was bleached. The coloring and bleaching cycle could be repeated many times.

EXAMPLE 3

Preparation of 5',7'-dimethoxy-1',3',3'-trimethyl-6-nitro-8-methoxyspiro[2H-1-benzothiopyran-2,2'-indoline]

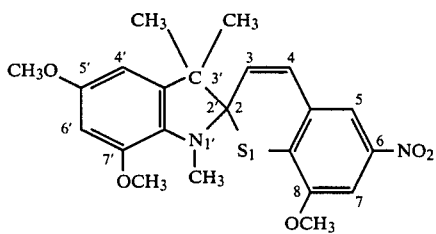

5,7-dimethoxy-1,3,3-trimethyl-2-methyleneindoline of the following formula, which was one of starting materials,

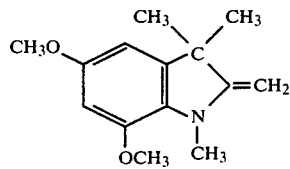

was prepared as follows. 20 g of 3-bromo-3-methyl-2-butanone and 55.5 g of 2,4-dimethoxyaniline were heated at 140° C. for 1 hour, which was then extracted with chloroform. The chloroform phase was treated with a diluted hydrochloric acid solution of 18 cc of concentrated hydrochloric acid diluted with 200 cc of water. An excess of the dimethoxyaniline was removed from the solution, followed by distilling under reduced pressure to obtain 16.4 g of 5,7-dimethoxy-2,3,3-trimethylindolenine (yield 62%, boiling point 107° C.0.2 mmHg).

5 g of the indolenine and 4 g of methyl iodide was dissolved in 5 cc of methanol, which was hermetically sealed and reacted at 110° C. for 2 hours. The resulting powder product was washed with ether, dried and treated with NaOH to obtain 3.7 g (yield 70%) of 5,7-dimethoxy-1,3,3-trimethyl-2-methyleneindoline.

3.4 g of the indoline and 3.2 g of the 3-methoxy-5-nitrosalicylaldehyde obtained in Example 2 were reacted in the same manner as in Example 2 to obtain 4.3 g of intended 5',7'-dimethoxy-1',3',3'-trimethyl-6-nitro-8-methoxyspiro[2H-1-benzothiopyran-2,2'-indoline] (yield 69%, melting point 131° C.).

The compound was identified by the proton-NMR spectroscopy. The DMF solution of the compound exhibited a coloring and bleaching phenomenon similar to the compound of Example 2.

EXAMPLE 4

Preparation of 5'-methoxy-1',3',3'-trimethyl-6-nitro-8-chlorospiro[2H-1-benzothiopyran-2,2'-indoline]

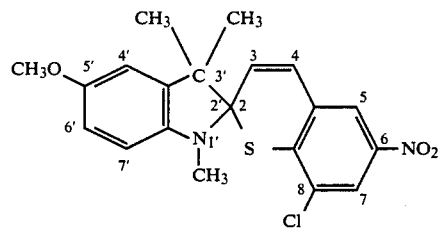

3-chloro-5-nitrothiosalicylaldehyde of the following formula, which was one of starting materials,

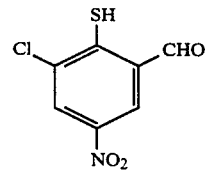

was prepared as follows. 10 g of 3-chloro-5-nitrosalicylaldehyde was dissolved in 300 cc of DMF, to which was added 1.2 g of NaH under ice-cooling conditions. When generation of hydrogen stopped, a solution of 8 g of dimethylthiocarbamoyl chloride in 10 cc of DMF was added at a time, followed by reaction at 40° C. for 15 minutes and then at 80° C. for 1 hour. After cooling, iced water was added to the reaction mixture and the resulting crystals were filtered and recrystallized from benzene-ethanol. 7.3 g (yield 51%) of a compound of the following formula was obtained.

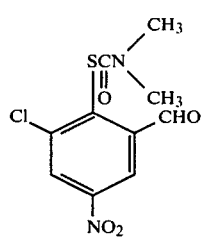

5 g of the compound was dissolved in 25 cc of ethanol, to which was added 23.5 cc of 4N NaOH aqueous solution, followed by reaction at a normal temperature for 2 hours while blowing $N_2$ gas. The reaction mixture was rendered acidic by the use of dilute hydrochloric acid and the resulting yellow crystals were filtered and dried to obtain 3.72 g of 3-chloro-5-nitrothiosalicylaldehyde (yield 99%, melting point 84°–89° C.).

2.5 g of the salicylldehyde and 2.5 g of 5-methoxy-1,3,3-trimethyl-2-methyleneindoline were reacted in the same manner as in Example 2 and the resulting product was separated to obtain 3.3 g of intended 5'-methoxy-1',3',3'-trimethyl-6-nitro-8-chlorospiro[2H-1-benzothiopyran-2,2'-indoline] (yield 67%). The melting point was 168°–169° C. The compound was identified by the proton-NMR spectroscopy.

4 parts by weight of the thiopyran-type spiropyran compound obtained in this example and 10 parts by weight of vinyl chloride-vinylidene chloride copolymer (Denka Vinyl #1000W, by Denki Chem. Ind. Co., Ltd.) were dissolved in 100 parts by weight of a mixture of tetrahydrofuran and cyclohexanone in a mixing ratio by volume of 1:1. The solution was spinner coated onto a quartz glass plate and dried in vacuo at 80° C. for 2 hours to obtain a sample having a 1 micron thick photosensitive film. The sample was irradiated with ultraviolet light of about 360 nm from a 500 W super high pressure mercury lamp (made by Ushio Electric Co., Ltd.) through a UV-360 filter (made by Toshiba Corp.), whereupon green color was developed in the sample. The colored sample had an absorption maximum wavelength of 650 nm, at which a saturation absorbance was 0.6. The absorbance was found to be 0.43 at 720 nm and 0.14 at 780 nm. The colored sample was bleached when heated to 80° C. and was again colored upon irradiation of ultraviolet light. This phenomenon could be brought about repeatedly many times.

EXAMPLE 5

Preparation of 5'-dimethylamino-1',3',3'-trimethyl-6-nitrospiro[2H-1-benzothiopyran-2,2'-indoline]

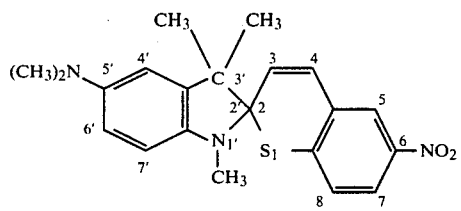

Starting 5-dimethylamino-1,3,3-trimethyl-2-methyleneindoline of the following formula

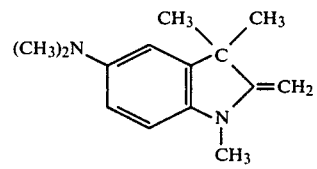

was prepared as follows. 3.74 g of 5-amino-2,3,3-trimethylindolenine, 6.61 g of 1,2,2,6,6-pentamethylpiperidine and 18.27 g of methyl iodide were dissolved in 40 cc of DMF, which was allowed to stand at room temperature for 15 hours. The resulting crystals were washed with an acetone solution containing 6% DMF and then with acetone, followed by drying and adding 150 cc of n-propyl alcohol containing 23.5 g of sodium. The mixture was refluxed for demethylation over 17 hours and the n-propyl alcohol was removed under reduced pressure. Water was added to the reaction solution, which was extracted with ether to obtain 4.21 g of 5-dimethylamino-1,3,3-trimethyl-2-methyleneindoline (yield 91%).

3 g of the thus obtained indoline and 3 g of the 5-nitrothiosalicylaldehyde obtained in Example 1 were heated in 40 cc of ethanol for 4 hours, followed by treating in the same manner as in Example 2 to obtain 2.4 g of intended 5'-dimethylamino-1',3',3'-trimethyl-6-nitrospiro[2H-1-benzothiopyran-2,2'-indoline] (yield 45%, melting point 166.5° C.–167° C.). For identification, the proton-NMR spectroscopy was used.

The compound of this example was used to make a polymer film in the same manner as in Example 4. When the film sample was irradiated by UV light, blackish purple color developed. The absorption spectra were as follows: the absorption maximum wavelength was 620 nm and the saturation absorbance at the wavelength (at the time when the UV light was irradiated and an absorbance of the colored sample reached a saturation) was 0.62. The absorbance was 0.42 at 720 nm and 0.13 at 780 nm. When the colored photosensitive film sample was heated to 80° C., an absorption of light having a wavelength over 700 nm disappeared. This absorption reappeared upon irradiation of UV light. The color formation of the sample was very stable.

Thiopyran-type spiropyran compounds having various substituents as indicated in Table 1 were prepared in the same manner as in Examples 1 through 5. These compounds were identified by the proton-NMR spectroscopy. The compounds were used to make photosensitive films in the same manner as in Example 4. The films were irradiated to such an extent that color formation reached a saturation. The results are shown in Table 1. Absorbances at certain wavelengths were those values of 1 micron thick photosensitive films. From the results, it will be seen that the compounds of the present invention have high absorptions at wavelengths over 700 nm.

As will be understood from the foregoing, the thiopyran-base spiropyran photochromic compounds of the present invention in which the oxygen atom in the benzopyran structure of a known spiropyran compound is substituted with sulfur atom and which have $NO_2$ group at the 6 position become sensitive to light of a longer wavelength by about 100 nm than known spiropyran compound and have high absorption characteristic with respect to a wavelength over 700 nm.

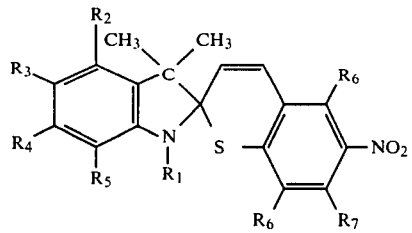

in which $R_1$ represents an alkyl group having 1 to 20 carbon atoms, $R_2$, $R_3$, $R_4$ and $R_5$ independently represent an alkyl group having 1 to 5 carbon atoms, an alkoxy group having 1 to 5 carbon atoms, a halogen atom, a nitro group, a cyano group or a dimethylamino

TABLE 1

| Substituent | | | | | | | | Melting point (°C.) | Absorption maximum wavelength $\lambda_{max}$ (nm) | Absorbance | | |
|---|---|---|---|---|---|---|---|---|---|---|---|---|
| $R_1$ | $R_2$ | $R_3$ | $R_4$ | $R_5$ | $R_6$ | $R_7$ | $R_8$ | | | $\lambda_{max}$ | 720 nm | 780 nm |
| $CH_3$ | H | H | H | H | H | H | H | 178–179 | 680 | 0.48 | 0.43 | 0.22 |
| $CH_3$ | H | $NO_2$ | H | H | H | H | H | 221–223 | 750 | 0.24 | 0.23 | 0.22 |
| $CH_3$ | H | Cl | H | H | H | H | H | 139–139.5 | 690 | 0.53 | 0.51 | 0.33 |
| $CH_3$ | H | $CH_3$ | H | H | H | H | H | 137–138 | 670 | 0.44 | 0.37 | 0.19 |
| $CH_3$ | H | $OCH_3$ | H | H | H | H | H | 160–162 | 660 | 0.57 | 0.47 | 0.19 |
| $CH_3$ | H | $OCH_3$ | H | H | H | H | $OCH_3$ | 165–166 | 690 | 0.45 | 0.42 | 0.25 |
| $C_6H_{13}$ | H | $OCH_3$ | H | H | H | H | $OCH_3$ | 97–98 | 690 | 0.56 | 0.52 | 0.29 |
| $CH_3$ | H | $CH_3$ | H | H | H | H | $OCH_3$ | 224–225 | 695 | 0.53 | 0.51 | 0.33 |
| $CH_3$ | H | H | H | H | H | H | $OCH_3$ | 180–181 | 700 | 0.55 | 0.54 | 0.37 |
| $CH_3$ | H | Cl | H | H | H | H | $OCH_3$ | 239–240 | 720 | 0.53 | 0.53 | 0.43 |
| $CH_3$ | H | $NO_2$ | H | H | H | H | $OCH_3$ | 242 | 770 | 0.18 | 0.16 | 0.18 |
| $CH_3$ | H | $OCH_3$ | H | $OCH_3$ | H | H | $OCH_3$ | 131 | 675 | 0.34 | 0.28 | 0.15 |
| $C_6H_{13}$ | H | $OCH_3$ | H | $OCH_3$ | H | H | $OCH_3$ | 93 | 675 | 0.55 | 0.45 | 0.20 |
| $CH_3$ | H | $OCH_3$ | H | H | H | H | Cl | 168–169 | 650 | 0.60 | 0.43 | 0.14 |
| $CH_3$ | H | $OCH_3$ | H | H | H | H | Br | 193–194 | 645 | 0.64 | 0.42 | 0.14 |
| $CH_3$ | H | $OCH_3$ | H | H | H | H | $CH_3$ | 177–178 | 675 | 0.52 | 0.47 | 0.22 |
| $CH_3$ | H | $OCH_3$ | H | H | H | $OCH_3$ | H | 193–194 | 650 | 0.59 | 0.38 | 0.09 |
| $C_6H_{13}$ | H | $OCH_3$ | H | H | Cl | H | Cl | 96 | 610 | 0.57 | 0.13 | 0.03 |
| $C_6H_{13}$ | H | $OCH_3$ | H | H | H | H | Cl | 110 | 650 | 0.70 | 0.45 | 0.14 |
| $CH_3$ | H | $N(CH_3)_2$ | H | H | H | H | H | 167 | 620 | 0.62 | 0.42 | 0.13 |
| $CH_3$ | H | $N(CH_3)_2$ | H | H | H | H | $CH_3$ | 156 | 640 | 0.31 | 0.36 | 0.13 |
| $CH_3$ | H | $N(CH_3)_2$ | H | H | H | H | $OCH_3$ | 187 | 670 | 0.30 | 0.24 | 0.12 |
| $CH_3$ | H | $N(CH_3)_2$ | H | Cl | H | H | H | 170–172 | 670 | 0.37 | 0.30 | 0.15 |
| $CH_3$ | H | $N(CH_3)_2$ | H | Cl | H | H | $OCH_3$ | 204–206 | 710 | 0.16 | 0.16 | 0.11 |
| $C_6H_{13}$ | H | $OCH_3$ | H | H | H | H | H | Oily, viscous matter | 665 | 0.50 | 0.40 | 0.16 |

What is claimed is:

1. A photosensitive composition comprising 3 to 50 wt. % of a photochromic compound of the general formula group, and $R_6$, $R_7$ and $R_8$ independently represent a hydrogen atom, an alkyl group having 1 to 5 carbon atoms, an alkoxy group having 1 to 5 carbon atoms, or a halogen atom, and correspondingly 97 to 50 wt. % of a film-forming polymer.

2. A photosensitive composition according to claim 1, wherein $R_1$ represents an alkyl group having 1 to 10 carbon atoms, and $R_2$ and $R_4$ through $R_8$ independently represent a hydrogen atom.

3. A photosensitive composition according to claim 1 or 2, wherein said polymer is a chlorine-containing polymer.

4. A photosensitive material comprising a film of the composition as claimed in claim 1 or 2.

* * * * *